(12) United States Patent
Markovitz et al.

(10) Patent No.: US 12,138,060 B2
(45) Date of Patent: Nov. 12, 2024

(54) SYSTEM AND METHOD FOR CARDIAC MAPPING

(71) Applicant: St. Jude Medical Cardiology Division, Inc., St. Paul, MN (US)

(72) Inventors: Craig Markovitz, Mahtomedi, MN (US); Jan O. Mangual-Soto, Rho (IT); Chunlan Jiang, Northridge, CA (US); Louis-Philippe Richer, Quebec (CA); Cyrille Casset, Saint Selve (FR)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 524 days.

(21) Appl. No.: 17/594,139

(22) PCT Filed: Mar. 2, 2020

(86) PCT No.: PCT/US2020/020662
§ 371 (c)(1),
(2) Date: Oct. 4, 2021

(87) PCT Pub. No.: WO2020/205128
PCT Pub. Date: Oct. 8, 2020

(65) Prior Publication Data
US 2022/0167899 A1 Jun. 2, 2022

Related U.S. Application Data

(60) Provisional application No. 62/829,422, filed on Apr. 4, 2019.

(51) Int. Cl.
*A61B 5/287* (2021.01)
*A61B 5/00* (2006.01)
(Continued)

(52) U.S. Cl.
CPC .............. *A61B 5/287* (2021.01); *A61B 5/061* (2013.01); *A61B 5/367* (2021.01); *A61B 5/7435* (2013.01)

(58) Field of Classification Search
None
See application file for complete search history.

(56) References Cited

U.S. PATENT DOCUMENTS 5,697,377 A 12/1997 Wittkampf
5,916,163 A * 6/1999 Panescu ............... A61B 5/7435
600/374
(Continued)

OTHER PUBLICATIONS

International Search Report and Written Opinion for International Application No. PCT/US2020/020662 (published as WO 2020/205128), dated Jun. 8, 2020.

*Primary Examiner* — Michael W Kahelin
*Assistant Examiner* — Luke M Stanley
(74) *Attorney, Agent, or Firm* — Wiley Rein LLP

(57) ABSTRACT

A method of generating a map of a portion of a patient's anatomy using an electroanatomical mapping system includes separating an anatomical region (e.g., the heart) into an inclusion region (e.g., the left atrium) and an exclusion region (e.g., the left ventricle) by defining a boundary surface (e.g., along the mitral valve). A label electrode carried by a multi-electrode catheter can be defined and used to determine whether or not to add an electrophysiology data point collected using the multi-electrode catheter to the map. In particular, electrophysiology data points can be added to the map of the portion of the patient's anatomy when they are collected with the label electrode within the inclusion region. Positions of the label electrode can also be used to define the boundary surface. Alerts can also be provided when the label electrode crosses the boundary surface and enters the exclusion region.

14 Claims, 5 Drawing Sheets

(51) Int. Cl.
*A61B 5/06* (2006.01)
*A61B 5/367* (2021.01)

(56) References Cited

U.S. PATENT DOCUMENTS

| | | |
|---|---|---|
| 5,983,126 A | 11/1999 | Wittkampf |
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 7,885,707 B2 | 2/2011 | Hauck |
| 10,231,637 B2 | 3/2019 | Voth et al. |
| 10,542,888 B2 | 1/2020 | Zeidan et al. |
| 10,758,137 B2 | 9/2020 | Deno et al. |
| 2010/0286550 A1* | 11/2010 | Harlev ............... A61B 5/0538 600/547 |
| 2010/0312095 A1* | 12/2010 | Jenkins ............... A61B 5/418 600/411 |
| 2015/0057507 A1 | 2/2015 | Koyrakh et al. |
| 2015/0313555 A1* | 11/2015 | Nabutovsky ......... A61B 5/316 600/374 |
| 2015/0317448 A1* | 11/2015 | Razavi ................ A61B 5/283 702/19 |
| 2015/0366481 A1* | 12/2015 | Voth .................. A61B 5/333 600/523 |
| 2016/0113582 A1* | 4/2016 | Altmann .............. A61M 25/09 606/41 |
| 2016/0317094 A1 | 11/2016 | Byrd et al. |

\* cited by examiner

SYSTEM AND METHOD FOR CARDIAC MAPPING

CROSS-REFERENCE TO RELATED APPLICATIONS

This application claims the benefit of U.S. provisional application No. 62/829,422, filed 4 Apr. 2019, which is hereby incorporated by reference as though fully set forth herein.

BACKGROUND

The present disclosure relates generally to cardiac mapping, such as may be performed in cardiac diagnostic and therapeutic procedures. In particular, the present disclosure relates to systems, apparatuses, and methods for generating cardiac geometry and/or electrophysiology maps from data collected by a roving electrophysiology probe, such as a high density ("HD") grid catheter or other multi-electrode device.

Cardiac mapping, including the generation of cardiac geometries and electrocardiographic mapping, is a part of numerous cardiac diagnostic and therapeutic procedures. As the complexity of such procedures increases, however, the geometries and electrophysiology maps utilized must increase in quality, in density, and in the rapidity and ease with which they can be generated.

It is known to use a multi-electrode catheter, such as an HD grid catheter, to gather data points used in the creation of cardiac geometries and/or electrophysiology maps. During an electrophysiology study, however, the catheter (or a portion thereof) may move into a region other than the region of interest. For instance, when mapping the left atrium, the catheter may inadvertently pass through the mitral valve into the left ventricle or deeper into the pulmonary veins than desirable for the atrial map.

BRIEF SUMMARY

Disclosed herein is a method of generating a map of a portion of a patient's anatomy, including the following steps: receiving, at an electroanatomical mapping system, a definition of a boundary surface that separates an anatomical region into a first anatomical sub-region and a second anatomical sub-region; receiving, at the electroanatomical mapping system, a definition of one of the first anatomical sub-region and the second anatomical sub-region as a region of interest; receiving, at the electroanatomical mapping system, an electrophysiology data point collected using a multi-electrode catheter; and the electroanatomical mapping system adding the electrophysiology data point to the map of the portion of the patient's anatomy when the electrophysiology data point is within the region of interest.

In embodiments of the disclosure, the step of receiving, at the electroanatomical mapping system, a definition of a boundary surface includes: receiving, at the electroanatomical mapping system, a geometric model of the anatomical region; receiving, at the electroanatomical mapping system, a definition of three points within the geometric model of the anatomical mapping system that define the boundary surface.

In other embodiments of the disclosure, the step of receiving, at the electroanatomical mapping system, a definition of a boundary surface includes: receiving, at the electroanatomical mapping system, a definition of a first point outside of the region of interest; receiving, at the electroanatomical mapping system, a definition of a second point within the region of interest; the electroanatomical mapping system defining a vector connecting the first point and the second point; and the electroanatomical mapping system defining the boundary surface as a boundary plane perpendicular to the vector and including the first point. The method can also include receiving, at the electroanatomical mapping system, an input to displace the boundary plane along the vector and/or an input to change an orientation of the boundary plane relative to the vector.

According to aspects of the disclosure, the step of receiving, at the electroanatomical mapping system, a definition of a first point outside of the region of interest includes: receiving, at the electroanatomical mapping system, an input that the multi-electrode catheter has exited the region of interest; and the electroanatomical mapping system defining a first location of a distal-most electrode on the multi-electrode catheter as the first point outside the region of interest. Analogously, it is contemplated that the step of receiving, at the electroanatomical mapping system, a definition of a second point within the region of interest can include: receiving, at the electroanatomical mapping system, an input that the multi-electrode catheter has re-entered the region of interest; and the electroanatomical mapping system defining a second location of the distal-most electrode on the multi-electrode catheter as the second point within the region of interest.

The step of the electroanatomical mapping system adding the electrophysiology data point to the map of the portion of the patient's anatomy when the electrophysiology data point is collected within the region of interest can include the electroanatomical mapping system adding the electrophysiology data point to the map of the portion of the patient's anatomy when a distal-most electrode on the multi-electrode catheter is within the region of interest.

It is also contemplated that the method can include the electroanatomical mapping system outputting an alert when the multi-electrode catheter exits the region of interest.

Also disclosed herein is a method of generating a map of a portion of a patient's anatomy. The method includes: an electroanatomical mapping system defining a boundary surface that separates an anatomical region into an inclusion region and an exclusion region; the electroanatomical mapping system defining a label electrode carried by a multi-electrode catheter; the electroanatomical mapping system receiving an electrophysiology data point collected using the multi-electrode catheter; and the electroanatomical mapping system adding the electrophysiology data point to the map of the portion of the patient's anatomy when the electrophysiology data point is collected with the label electrode within the inclusion region.

In embodiments of the disclosure, the step of the electroanatomical mapping system defining a label electrode carried by a multi-electrode catheter includes the electroanatomical mapping system defining a distal-most electrode carried by the multi-electrode catheter as the label electrode. Alternatively, the step of the electroanatomical mapping system defining a label electrode carried by a multi-electrode catheter includes the electroanatomical mapping system receiving a user input defining the label electrode.

According to aspects of the disclosure, the step of an electroanatomical mapping system defining a boundary surface that separates an anatomical region into an inclusion region and an exclusion region includes: the electroanatomical mapping system receiving a user input of three points within the anatomical region; and the electroanatomical mapping system defining the boundary surface as a boundary plane that includes the three points.

In other aspects of the disclosure, the step of an electroanatomical mapping system defining a boundary surface that separates an anatomical region into an inclusion region and an exclusion region includes: the electroanatomical mapping system receiving a user input of a first position of the label electrode and a second position of the label electrode; and the electroanatomical mapping system defining a plane perpendicular to a vector connecting the first position of the label electrode and the second position of the label electrode as the boundary surface. The plane can include one of the first position of the label electrode and the second position of the label electrode. The electroanatomical mapping system can also receive a user input selecting a position of the plane along the vector connecting the first position of the label electrode and the second position of the label electrode and/or a user input resetting an orientation of the plane relative to the vector connecting the first position of the label electrode and the second position of the label electrode.

The electroanatomical mapping system can optionally output an alert when the label electrode enters the exclusion region.

The instant disclosure also provides an electroanatomical mapping system for generating a map of a portion of a patient's anatomy, including an inclusion processor configured to: define a boundary surface that separates an anatomical region into an inclusion region and an exclusion region; identify whether a label electrode carried by a multi-electrode catheter is within the inclusion region or the exclusion region; and add a plurality of electrophysiology data points collected by the multi-electrode catheter when the label electrode is within the inclusion region to the map of the portion of the patient's anatomy. The inclusion processor can be configured to define the boundary surface from a first position of the label electrode and a second position of the label electrode, wherein only one of the first position of the label electrode and the second position of the label electrode is within the inclusion region.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for generating anatomical maps, such as surface geometries (anatomical models) and electrophysiology maps. For purposes of illustration, aspects of the disclosure will be described with reference to cardiac electrophysiology procedures. More specifically, aspects of the disclosure will be described in the context of the creation of cardiac geometries and cardiac electrophysiology maps from electrophysiology data points collected using a high density (HD) grid catheter, such as the Advisor™ HD grid mapping catheter from Abbott Laboratories (Abbott Park, Illinois), in conjunction with an electroanatomical mapping system, such as the EnSite Precision™ cardiac mapping system, also from Abbott Laboratories. Even more specifically, aspects of the disclosure will be described with reference to atrial mapping. Those of ordinary skill in the art will understand, however, how to apply the teachings herein to good advantage in other contexts and/or with respect to other devices.

Figure 1:
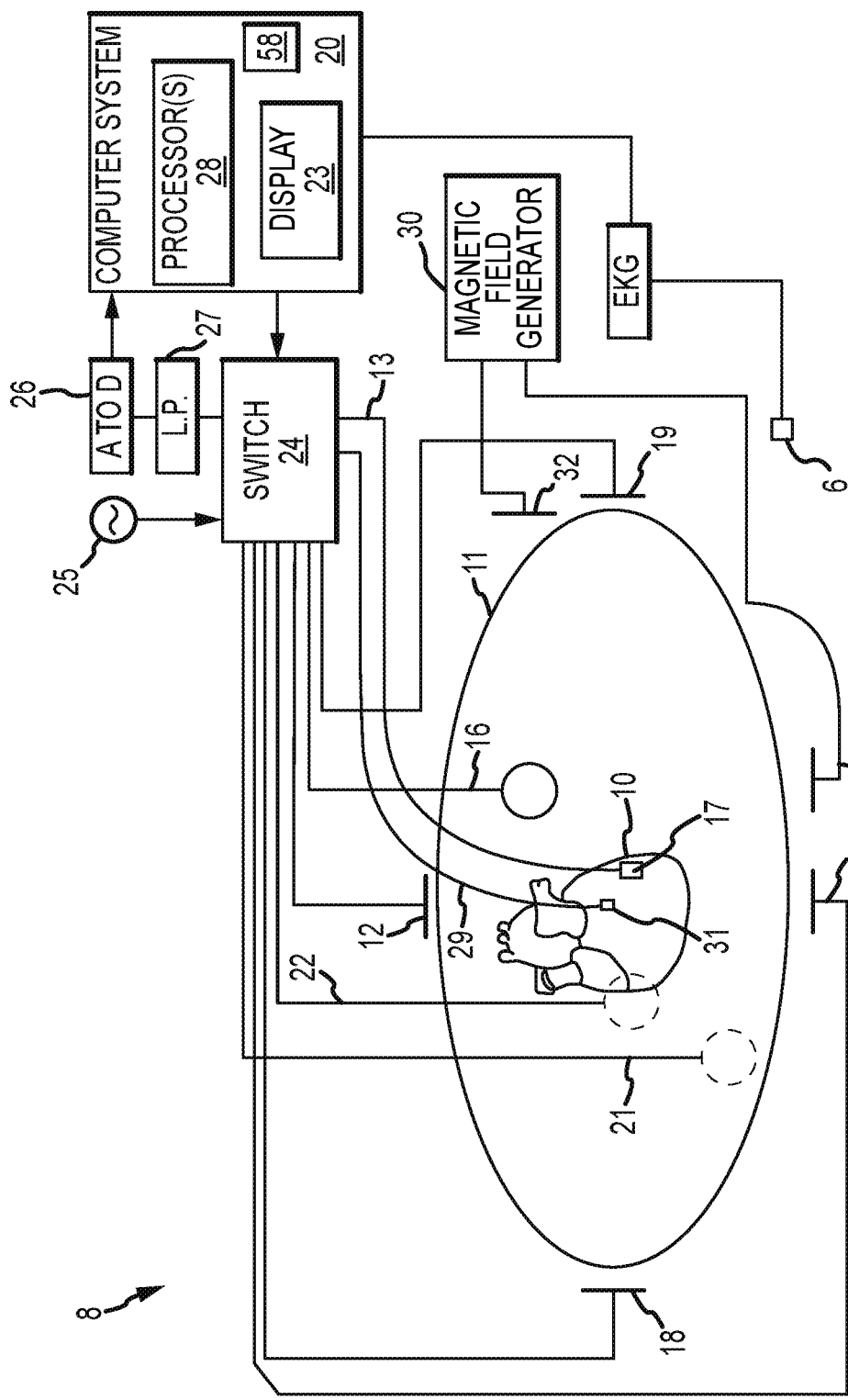
FIG. 1 is a schematic diagram of an exemplary electroanatomical mapping system.

FIG. 1 shows a schematic diagram of an exemplary electroanatomical mapping system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. In other embodiments, system 8 may utilize a single catheter that includes multiple (e.g., eight) splines, each of which in turn includes multiple (e.g., eight) electrodes.

Figure 2:
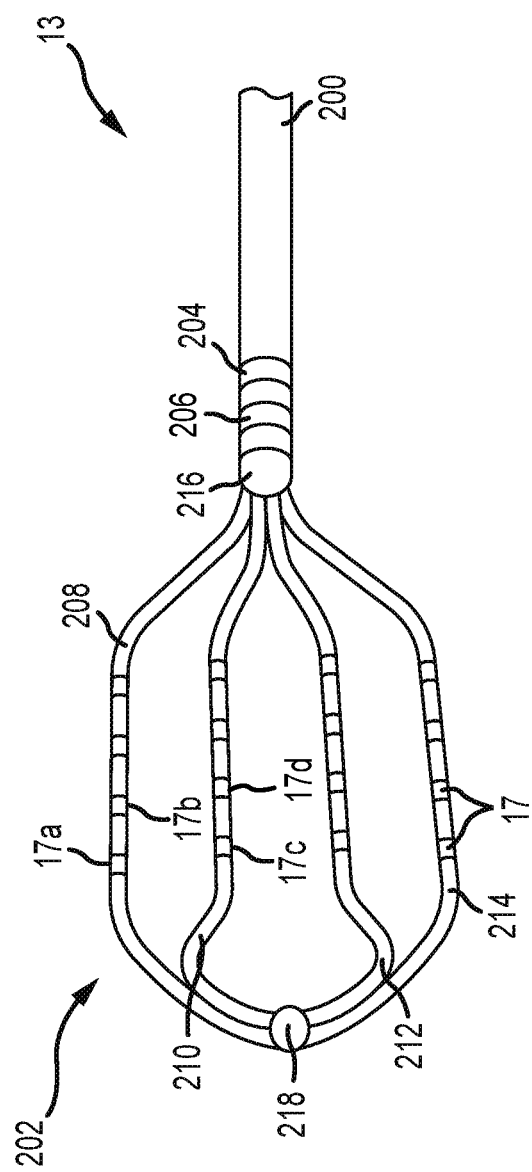
FIG. 2 depicts an exemplary catheter that can be used in connection with aspects of the instant disclosure.

The foregoing embodiments are merely exemplary, however, and any number of electrodes and/or catheters may be used. For example, for purposes of this disclosure, a segment of an exemplary multi-electrode catheter, and in particular an HD grid catheter, is shown in FIG. 2. HD grid catheter 13 includes a catheter body 200 coupled to a paddle 202. Catheter body 200 can further include first and second body electrodes 204, 206, respectively. Paddle 202 can include a first spline 208, a second spline 210, a third spline 212, and a fourth spline 214, which are coupled to catheter body 200 by a proximal coupler 216 and to each other by a distal coupler 218. In one embodiment, first spline 208 and fourth spline 214 can be one continuous segment and second spline 210 and third spline 212 can be another continuous segment. In other embodiments, the various splines 208, 210, 212, 214 can be separate segments coupled to each other (e.g., by proximal and distal couplers 216, 218, respectively). It should be understood that HD catheter 13 can include any number of splines; the four-spline arrangement shown in FIG. 2 is merely exemplary.

As described above, splines 208, 210, 212, 214 can include any number of electrodes 17; in FIG. 2, sixteen electrodes 17 are shown arranged in a four-by-four array. It should also be understood that electrodes 17 can be evenly and/or unevenly spaced, as measured both along and between splines 208, 210, 212, 214. For purposes of easy reference in this description, FIG. 3A provides alphanumeric labels for electrodes 17.

As those of ordinary skill in the art will recognize, any two neighboring electrodes 17 define a bipole. Thus, the 16 electrodes 17 on catheter 13 define a total of 42 bipoles—12 along splines (e.g., between electrodes 17a and 17b, or between electrodes 17c and 17d), 12 across splines (e.g., between electrodes 17a and 17c, or between electrodes 17b and 17d), and 18 diagonally between splines (e.g., between electrodes 17a and 17d, or between electrodes 17b and 17c).

Figure 3B:
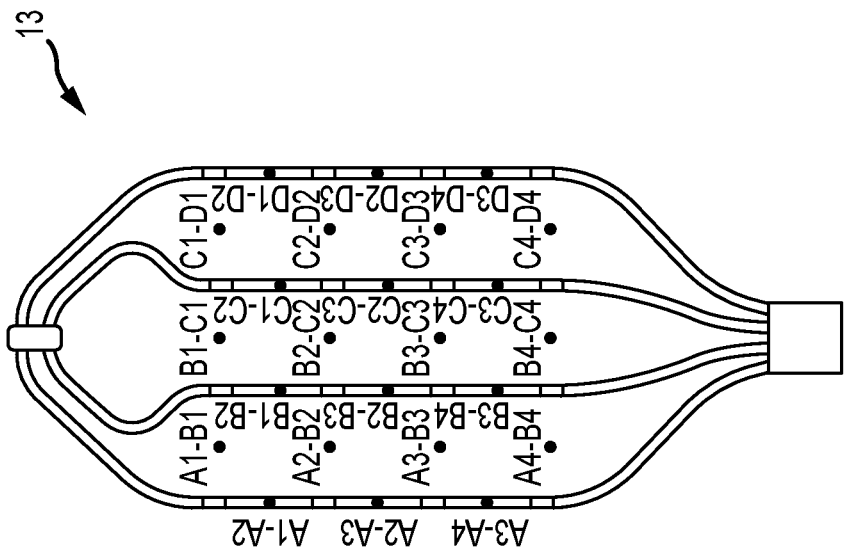
FIGS. 3A and 3B provide alphanumeric labeling conventions for electrodes carried by a multi-electrode catheter and the bipoles associated therewith.
Figure 3A:
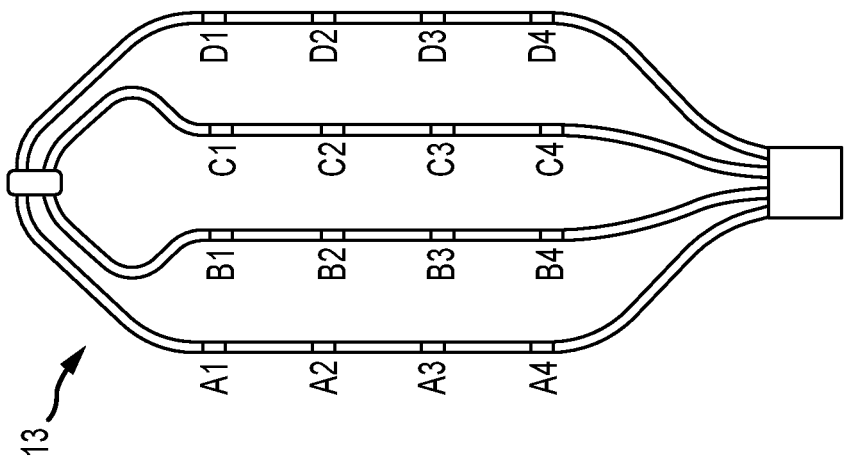

For ease of reference in this description, FIG. 3B provides alphanumeric labels for the along- and across-spline bipoles. FIG. 3B omits alphanumeric labels for the diagonal bipoles, but this is only for the sake of clarity in the illustration. It is expressly contemplated that the teachings herein can also be applied with respect to the diagonal bipoles.

Any bipole can, in turn, be used to generate a bipolar electrogram according to techniques that will be familiar to those of ordinary skill in the art. Moreover, these bipolar electrograms can be combined (e.g., linearly combined) to generate electrograms, again including activation timing information, in any direction of the plane of catheter 13 by computing an E-field loop for a clique of electrodes. U.S. application Ser. No. 15/953,155, which is hereby incorporated by reference as though fully set forth herein, discloses details of computing an E-field loop for a clique of electrodes on a HD grid catheter.

In any event, catheter 13 can be used to simultaneously collect a plurality of electrophysiology data points for the various bipoles defined by electrodes 17 thereon, with each such electrophysiology data point including both localization information (e.g., position and orientation of a selected bipole) and an electrogram signal for the selected bipole. For purposes of illustration, methods according to the instant disclosure will be described with reference to individual electrophysiology data points collected by catheter 13. It should be understood, however, that the teachings herein can be applied, in serial and/or in parallel, to multiple electrophysiology data points collected by catheter 13.

Catheter 13 (or multiple such catheters) are typically introduced into the heart and/or vasculature of the patient via one or more introducers and using familiar procedures. Indeed, various approaches to introduce catheter 13 into a patient's heart, such as transseptal approaches, will be familiar to those of ordinary skill in the art, and therefore need not be further described herein.

Since each electrode 17 lies within the patient, location data may be collected simultaneously for each electrode 17 by system 8. Similarly, each electrode 17 can be used to gather electrophysiological data from the cardiac surface (e.g., surface electrograms). The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation of a cardiac geometry and/or of cardiac electrical activity from the plurality of electrophysiology data points. Moreover, insofar as the ordinarily skilled artisan will appreciate how to create electrophysiology maps from electrophysiology data points, the aspects thereof will only be described herein to the extent necessary to understand the present disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In aspects of the disclosure, system 8 can be a hybrid system that incorporates both impedance-based (e.g., as described above) and magnetic-based localization capabilities. Thus, for example, system 8 can also include a magnetic source 30, which is coupled to one or more magnetic field generators. In the interest of clarity, only two magnetic field generators 32 and 33 are depicted in FIG. 1, but it should be understood that additional magnetic field generators (e.g., a total of six magnetic field generators, defining three generally orthogonal axes analogous to those defined by patch electrodes 12, 14, 16, 18, 19, and 22) can be used without departing from the scope of the present teachings. Likewise, those of ordinary skill in the art will appreciate that, for purposes of localizing catheter 13 within the magnetic fields so generated, can include one or more magnetic localization sensors (e.g., coils).

In some embodiments, system 8 is the EnSite™ Velocity™ or EnSite Precision™ cardiac mapping and visualization system of Abbott Laboratories. Other localization systems, however, may be used in connection with the present teachings, including for example the RHYTHMIA HDX™ mapping system of Boston Scientific Corporation (Marlborough, Massachusetts), the CARTO navigation and location system of Biosense Webster, Inc. (Irvine, California), the AURORA® system of Northern Digital Inc. (Waterloo, Ontario), Sterotaxis, Inc.'s NIOBE® Magnetic Navigation System (St. Louis, Missouri), as well as MediGuide™ Technology from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Aspects of the disclosure relate to generating anatomical maps (that is, maps of portions of a patient's anatomy, such as cardiac geometries and/or electrophysiology maps). Graphical representations of such maps can also be output, for example on display 23. System 8 can therefore include an inclusion module 58 that can be used to generate an anatomical map, and which may incorporate a mapping module to allow for graphical output thereof (e.g., to display 23).

Figure 4:
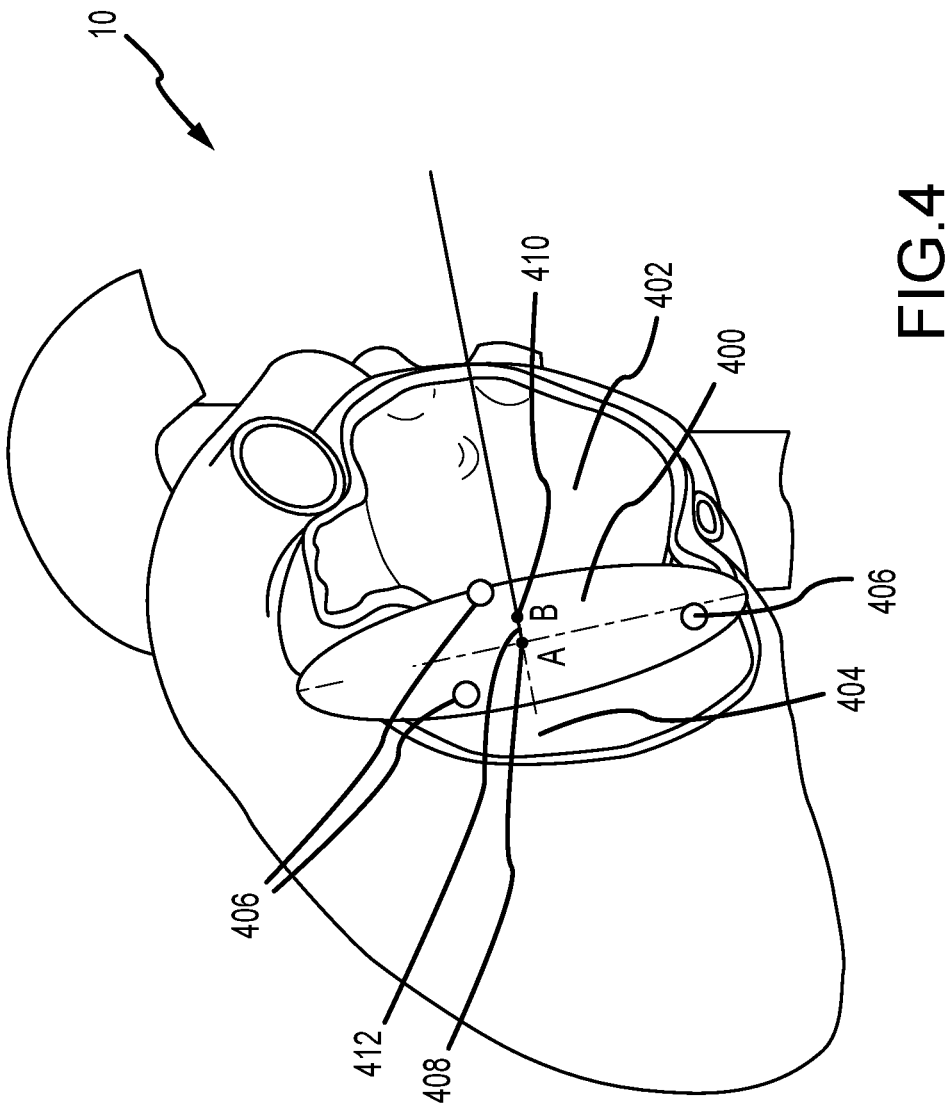
FIG. 4 illustrates aspects of the instant disclosure as applied to an anatomical model of a heart.

Aspects of the disclosure relate to the definition of boundary surfaces, such as boundary plane 400 illustrated in FIG. 4. Boundary plane 400 divides an anatomical region (e.g., heart 10) into a first sub-region (e.g., inclusion region 402, shown as the left atrium for purposes of illustration) and a second sub-region (e.g., exclusion region 404, shown as the left ventricle for purposes of illustration).

In embodiments of the disclosure, and in particular when a three-dimensional model of the cardiac geometry is available, a practitioner can define boundary plane 400 directly thereon. For instance, the practitioner can designate three points, such as three points 406 along the mitral valve, and system 8 can define boundary plane 400 therefrom. It is also contemplated that the practitioner can designate a greater number of points, and system 8 can define a best fit boundary plane 400, or a non-planar boundary surface, thereto.

In other embodiments of the disclosure, however, a three-dimensional model of the cardiac geometry may not be available. Accordingly, an exemplary method of defining a boundary surface (and, in particular, a boundary plane) according to another aspect of the present teachings will be explained with reference to the flowchart 500 of representative steps presented as FIG. 5. In some embodiments, for example, flowchart 500 may represent several exemplary steps that can be carried out by electroanatomical mapping system 8 of FIG. 1 (e.g., by processor 28 and/or inclusion module 58). It should be understood that the representative steps described below can be either hardware- or software-implemented. For the sake of explanation, the term "signal processor" is used herein to describe both hardware- and software-based implementations of the teachings herein.

In block 502, a label electrode is defined. The term "label electrode" is used herein to identify an electrode 17 on catheter 13 that is used as the basis for determining whether a collected electrophysiology data point is from the inclusion region, and thus should be added to an electrophysiology map, or from the exclusion region, and thus should not be added to the electrophysiology map.

Although an exemplary embodiment of the instant disclosure described in detail below utilizes a single label electrode—namely, a distal-most electrode—it should be understood that the teachings herein can be applied using other and/or additional electrodes on catheter 13. Indeed, it is contemplated that, in some embodiments of the disclosure, the practitioner can select the label electrode, such as through a graphical user interface generated by system 8 on display 23.

A point in exclusion region 404 (e.g., point 408 in FIG. 4) is defined in block 504, while a point in inclusion region 402 (e.g., point 410 in FIG. 4) is defined in block 506. According to aspects of the disclosure, points 408 and 410 are identified by a practitioner through a graphical user interface generated by system 8 on display 23.

For instance, when the practitioner observes on display 23 that the label electrode has passed into exclusion region 404, the practitioner can select a corresponding control on display 23, and the instantaneous location of the label electrode can be defined as point 408 within exclusion region 404. Similarly, when the practitioner observes on display 23 that the label electrode has reentered inclusion region 402, the practitioner can select a corresponding control on display 23, and the instantaneous location of the label electrode can be defined as point 410 within inclusion region 402.

In block 508, system 8 defines a vector (e.g., vector 412 in FIG. 4) connecting points 408 and 410, while, in block 510, system 8 defines boundary plane 400. In embodiments of the disclosure, boundary plane 400 is defined as a plane perpendicular to vector 412, and can further be defined to include one of points 408, 410—typically point 408, as point 410 falls within inclusion region 402. Of course, it is also contemplated that system 8 can accept input from a practitioner that adjusts the orientation of boundary plane 400 relative to vector 412 and/or the position of boundary plane 400 along vector 412 (that is, through what point between points 408, 410 does boundary plane 400 pass).

Figure 5:
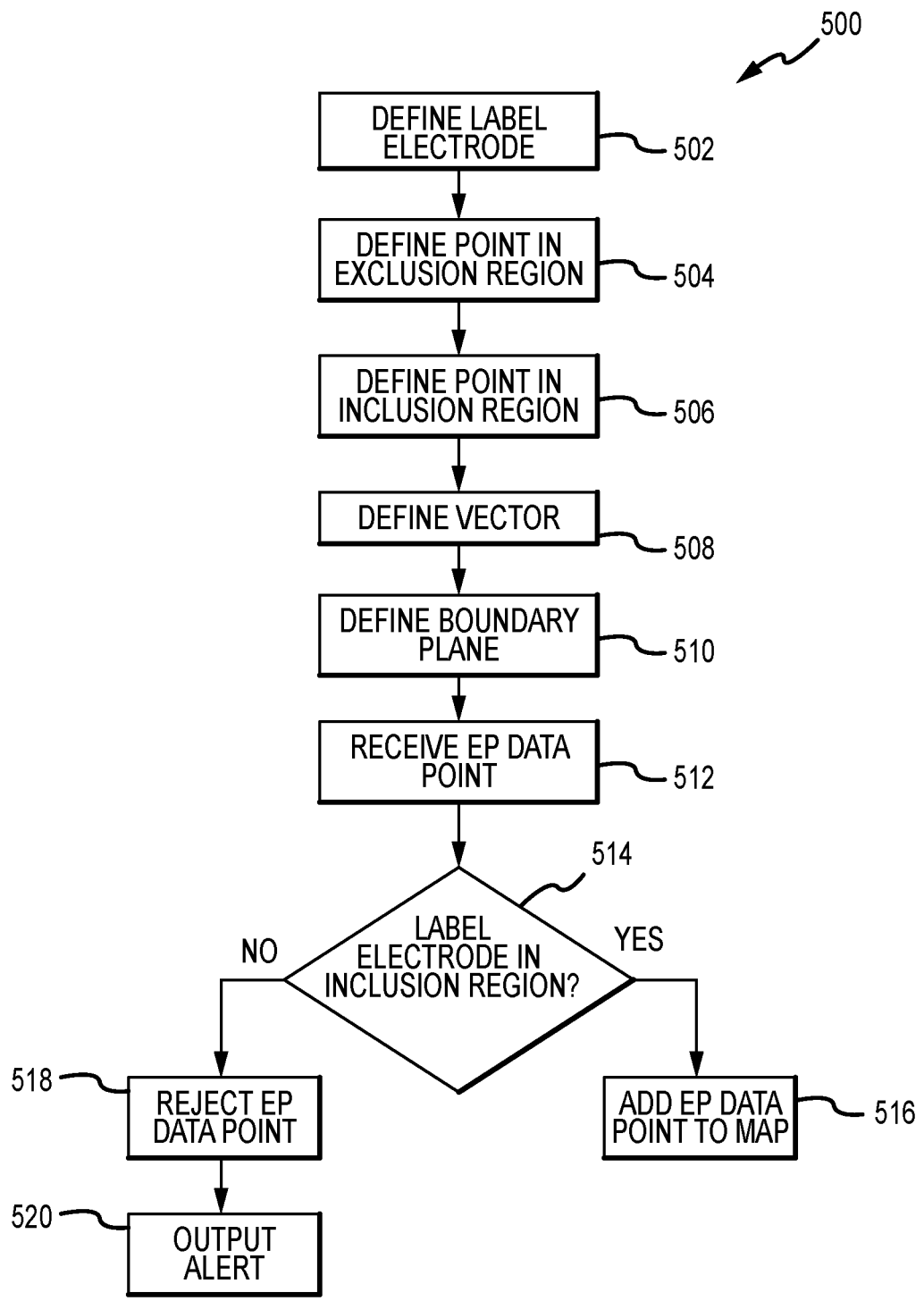
FIG. 5 is a flowchart of representative steps that can be carried out according to exemplary embodiments disclosed herein.

FIG. 5 further includes exemplary steps that can be carried out by electroanatomical mapping system 8 of FIG. 1 when mapping a portion of a patient's anatomy. Thus, in block 512, system 8 receives an electrophysiology data point from electrodes 17 carried by catheter 13 (e.g., one of the plurality of bipoles defined by electrodes 17 carried by catheter 13 as described above).

In decision block 514, system 8 evaluates whether the collected electrophysiology data point should be included within the map or excluded from the map (that is, whether the collected electrophysiology data point falls within inclusion region 402 or exclusion region 404). The position of the label electrode relative to boundary plane 400 can be used as a proxy for the position of the collected electrophysiology data point relative to boundary plane 400. Thus, for example, decision block 514 can evaluate whether the label electrode was within inclusion region 402 when the electrophysiology data point was collected. If so (the "YES" exit from decision block 514), then the electrophysiology data point under consideration can be added to the anatomical map in block 516.

If not (the "NO" exit from decision block 514), then the electrophysiology data point under consideration can be rejected/excluded from the anatomical map in block 518. It may also be desirable to alert the practitioner that catheter 13 (or a portion thereof) has crossed boundary plane 400 into exclusion region 404. Thus, system 8 can also output an alert (e.g., a visual, audible, and/or tactile indication) in block 520.

The process described above can be repeated for a plurality of electrophysiology data points, both collected sequentially (e.g., as catheter 13 moves through the patient's heart) and simultaneously (e.g., for multiple bipoles on catheter 13 for a single beat). Indeed, for simultaneously collected electrophysiology data points, the process described above can allow certain bipoles to be included and others to be excluded, for example through the use of a plurality of label electrodes that allow system 8 to recognize if only a portion of catheter 13 has crossed boundary plane 400 into exclusion region 404.

System 8 can also output a graphical representation of the anatomical map populated by the included electrophysiology data points (e.g., on display 23). As described above, the anatomical map can include a cardiac geometry and/or an electrophysiology map. Put another way, the teachings herein can be applied to generate the set of data points used to create a cardiac geometry model and/or the set of data points used to generate an electrophysiology map, which may in turn be output on a graphical representation of the cardiac geometry model.

Although several embodiments have been described above with a certain degree of particularity, those skilled in the art could make numerous alterations to the disclosed embodiments without departing from the spirit or scope of this invention.

For example, the teachings herein can be applied in real time (e.g., during an electrophysiology study) or during post-processing (e.g., to electrophysiology data points collected during an electrophysiology study performed at an earlier time).

As another example, the teachings herein can be applied to define multiple boundary planes, such as at the pulmonary vein ostia in addition to at the mitral valve.

As still another example, the teachings herein can be combined with the teachings of U.S. application Ser. No. 14/462,128 ("the '128 application"), which is hereby incorporated by reference as though fully set forth herein. When combined with the teachings of the '128 application, it may be computationally more efficient to apply the teachings of the '128 application to a collected electrophysiology data point before applying the instant teachings, but the opposite sequence would still be within the scope of the instant disclosure.

As a still further example, rather than discarding data points that are rejected/excluded at block 518, such points could instead be added to an alternative map (e.g., a ventricular geometry and/or electrophysiology map). In aspects of the disclosure, points that are rejected/excluded at block 518 may be added to such an alternative map if, and only if, they also satisfy one or more inclusion criteria (e.g., according to the teachings of the aforementioned '128 application).

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of generating a map of a portion of a patient's anatomy, comprising:
    receiving, at an electroanatomical mapping system, a definition of a boundary surface that separates an anatomical region into a first anatomical sub-region and a second anatomical sub-region;
    receiving, at the electroanatomical mapping system, a definition of one of the first anatomical sub-region and the second anatomical sub-region as a region of interest;
    receiving, at the electroanatomical mapping system, an electrophysiology data point collected using a multi-electrode catheter; and
    the electroanatomical mapping system adding the electrophysiology data point to the map of the portion of the patient's anatomy when the electrophysiology data point is within the region of interest,
    wherein receiving, at the electroanatomical mapping system, the definition of the boundary surface comprises:
        receiving, at the electroanatomical mapping system, a definition of a first point outside of the region of interest;
        receiving, at the electroanatomical mapping system, a definition of a second point within the region of interest;
        the electroanatomical mapping system defining a vector connecting the first point and the second point; and
        the electroanatomical mapping system defining the boundary surface as a boundary plane perpendicular to the vector and including the first point.

2. The method according to claim 1, further comprising receiving, at the electroanatomical mapping system, an input to displace the boundary plane along the vector.

3. The method according to claim 1, further comprising receiving, at the electroanatomical mapping system, an input to change an orientation of the boundary plane relative to the vector.

4. The method according to claim 1, wherein receiving, at the electroanatomical mapping system, a definition of a first point outside of the region of interest comprises:
    receiving, at the electroanatomical mapping system, an input that the multi-electrode catheter has exited the region of interest; and
    the electroanatomical mapping system defining a first location of a distal-most electrode on the multi-electrode catheter as the first point outside the region of interest.

5. The method according to claim 4, wherein receiving, at the electroanatomical mapping system, a definition of a second point within the region of interest comprises:
    receiving, at the electroanatomical mapping system, an input that the multi-electrode catheter has re-entered the region of interest; and
    the electroanatomical mapping system defining a second location of the distal-most electrode on the multi-electrode catheter as the second point within the region of interest.

6. The method according to claim 1, wherein the electroanatomical mapping system adding the electrophysiology data point to the map of the portion of the patient's anatomy when the electrophysiology data point is collected within the region of interest comprises the electroanatomical mapping system adding the electrophysiology data point to the map of the portion of the patient's anatomy when a distal-most electrode on the multi-electrode catheter is within the region of interest.

7. The method according to claim 1, further comprising the electroanatomical mapping system outputting an alert when the multi-electrode catheter exits the region of interest.

8. A method of generating a map of a portion of a patient's anatomy, comprising:
    an electroanatomical mapping system defining a boundary surface that separates an anatomical region into an inclusion region and an exclusion region;
    the electroanatomical mapping system defining a label electrode carried by a multi-electrode catheter;
    the electroanatomical mapping system receiving an electrophysiology data point collected using the multi-electrode catheter; and
    the electroanatomical mapping system adding the electrophysiology data point to the map of the portion of the patient's anatomy when the electrophysiology data point is collected with the label electrode within the inclusion region,
    wherein the electroanatomical mapping system defining a boundary surface that separates an anatomical region into an inclusion region and an exclusion region comprises:
        the electroanatomical mapping system receiving a user input of a first position of the label electrode and a second position of the label electrode; and
        the electroanatomical mapping system defining a plane perpendicular to a vector connecting the first position of the label electrode and the second position of the label electrode as the boundary surface.

9. The method according to claim 8, wherein the electroanatomical mapping system defining a label electrode carried by a multi-electrode catheter comprises the electroanatomical mapping system defining a distal-most electrode carried by the multi-electrode catheter as the label electrode.

10. The method according to claim 8, wherein the electroanatomical mapping system defining a label electrode carried by a multi-electrode catheter comprises the electroanatomical mapping system receiving a user input defining the label electrode.

11. The method according to claim 8, wherein the plane includes one of the first position of the label electrode and the second position of the label electrode.

12. The method according to claim 8, further comprising the electroanatomical mapping system receiving a user input selecting a position of the plane along the vector connecting the first position of the label electrode and the second position of the label electrode.

13. The method according to claim 8, further comprising the electroanatomical mapping system receiving a user input resetting an orientation of the plane relative to the vector connecting the first position of the label electrode and the second position of the label electrode.

14. The method according to claim 8, further comprising the electroanatomical mapping system outputting an alert when the label electrode enters the exclusion region.

\* \* \* \* \*